United States Patent
Guenin et al.

(10) Patent No.: US 6,793,915 B1
(45) Date of Patent: Sep. 21, 2004

(54) COOL AND DRY SOFT SOLID ANTIPERSPIRANT

(75) Inventors: Eric Guenin, Pennington, NJ (US); Jairajh Mattai, Piscataway, NJ (US); Suman Chopra, Dayton, NJ (US); Patricia Hall-Puzio, Succasunna, NJ (US); Rosemary Miano, Martinsville, NJ (US)

(73) Assignee: Colgate-Palmolive Company, NY, NY (US)

( * ) Notice: Subject to any disclaimer, the term of this patent is extended or adjusted under 35 U.S.C. 154(b) by 0 days.

(21) Appl. No.: 10/806,982

(22) Filed: Mar. 23, 2004

Related U.S. Application Data

(63) Continuation of application No. 10/178,576, filed on Jun. 24, 2002, now abandoned.

(51) Int. Cl.$^7$ .......................... A61K 7/32; A61K 31/74; A61K 7/00
(52) U.S. Cl. .................. 424/65; 424/78.02; 424/78.08; 424/400; 424/401
(58) Field of Search .............................. 424/65, 78.02, 424/78.08, 400, 401

(56) References Cited

U.S. PATENT DOCUMENTS

| | | |
|---|---|---|
| 4,661,476 A | 4/1987 | Lane et al. |
| 5,783,211 A | 7/1998 | Manzo et al. |

FOREIGN PATENT DOCUMENTS

| | | |
|---|---|---|
| EP | 0974332 | 7/1999 |
| WO | WO 98/43605 | 10/1998 |
| WO | WO 00/62737 | 10/2000 |
| WO | WO 01/66078 | 9/2001 |
| WO | WO 01/74306 | 10/2001 |
| WO | WO 03/030854 | 4/2003 |

*Primary Examiner*—Shelley A. Dodson
(74) *Attorney, Agent, or Firm*—Rosemary Miano

(57) ABSTRACT

A stable, high efficacy, low residue surfactant-free, soft solid cosmetic composition (especially an antiperspirant and/or deodorant) comprising: (a) 40–75 weight % of a volatile silicone; (b) 0.5–20 weight % of a non-emulsifying silicone elastomer; (c) 0.1–10 weight % of a of a superabsorbent powder with little or no tack upon wetting; (d) 0.01–0.5 weight % of a cooling agent selected from the group consisting of L-menthol; menthyl lactate; menthone glycerine; menthone glycerin acetal; (−)-isopulegol, N-ethyl-5-methyl-2-(1-methylethyl)-cyclohexanecarboxamide; N-ethyl-p-menthane-3-carboxzamide; 4-methyl-3-(1-pyrrolidinyl)-2[5H]-furanone; N,2,3-trimethyl-2-isopropylbutanamide; menthoxypropanediol; methanediol; and vanillyl butyl ether; (e) 0–20 weight % of an emollient or a mixture of two or more emollients; (f) 0–30 weight % of an antiperspirant active based on an anhydrous, buffer-free antiperspirant active; (g) 0–8 weight % of polyethylene beads having a particle size in the range of 5–40 microns and a density in the range of 0.91–0.98 g/cm$^3$; (h) 0–5 weight % fragrance; (j) 0–5 weight % of an antimicrobial agent; wherein the ratio of cooling agent to superabsorbent polymer is in the range of 1:50–1:2.

8 Claims, No Drawings

COOL AND DRY SOFT SOLID ANTIPERSPIRANT

This is a continuation of prior application Ser. No. 10/178,576 filed on Jun. 24, 2002 which application is now abandoned and is incorporated herein by reference.

FIELD OF THE INVENTION

This invention relates to antiperspirant soft solid products that provide superior cool and dry feeling in the underarm area even under stressful conditions. A related case is being filed on the same day as this case Serial Number not yet accorded.

BACKGROUND OF THE INVENTION

Soft solid products are described in U.S. Ser. No. 09/712,378, filed Nov. 14. 2000, entitled "Stable and Efficacious Soft Solid Products". The use of water absorbent materials is described in U.S. Ser. No. 09/971,978, filed Oct. 5, 2001, entitled Underarm Gel Products With Water Lock Component.

A number of formulations have been used that include some type of cooling agent such as menthol or mixtures of menthol with other ingredients. WO 00/42983 to Johnson & Johnson Consumer France describes a freshening cosmetic comprising 0.01–2 weight % menthol and 0.1–10 weight % menthyl lactate in a 1/1 to 1/10 ratio.

The cooling sensation is intensified by the presence of an aqueous phase or air flow. Thus, the presence of sweat in the underarm area may increase the cooling sensation to undesirable levels of coolness, and it has been a problem to control the type and amount of cooling in the underarm environment. It is an object of the present invention to create a composition that provides a controlled coolness in the underarm area so as to give preferred aesthetics.

SUMMARY OF THE INVENTION

The incorporation of cooling agents such as L-menthol; menthyl lactate; menthone glycerine; menthone glycerin acetal; (−)-isopulegol, N-ethyl-5-methyl-2-(1-methylethyl)-cyclohexanecarboxamide; N-ethyl-p-menthane-3-carboxzamide; 4-methyl-3-(1-pyrrolidinyl)-2[5H]-furanone; N,2,3-trimethyl-2-isopropylbutanamide (also known as 2-isopropyl-N,2,3-trimethylbutyramide); menthoxypropanediol; methanediol; vanillyl butyl ether; in an underarm product in combination with a selected superabsorbent material provides a superior product that balances a cooling effect with a dry sensation to give a constant dry cool perception in the underarm area over an extended period of time. The superabsorbent material in powder form acts to minimize the perception of wetness and acts as a water/liquid reservoir for the activation of the cooling agent. Since the selected cooling agents are activated by the presence of water, it is important to control the ratios of cooling agent and superabsorbent powder to achieve the desired effect.

It has been found that an improved, surfactant-free, soft solid cosmetic product may be made as a suspension formed with:

(a) a superabsorbent polymer;
(b) a selected cooling agent;
(c) a non-emulsifying elastomer;
(d) a volatile silicone; and optionally one or more of
(e) an emollient (which may also be a mixture of two or more emollients and which may include a non-volatile silicone);
(f) an effective amount of an antiperspirant active material to cause an antiperspirant and/or a deodorant effect; and
(g) polyethylene beads having a density in the range of 0.91–0.98 grams/cm$^3$ and a particle size in the range of 5–40 microns, wherein the polyethylene beads are used in an amount of at least 2% by weight based on the total weight of the composition.

The soft solid antiperspirant and/or deodorant product of this invention is an opaque product which leaves little or no white residue when applied and which exhibits improved efficacy and stability as compared to other formulations with different types of elastomers.

DETAILED DESCRIPTION OF THE INVENTION

This invention comprises an anhydrous, surfactant-free composition (no more than 1 weight % of added water (excluding any waters of hydration) and no more than 1% of any material that functions as a surfactant. The stable, high efficacy, low residue cosmetic compositions of this invention are made by combining:

(a) 40–75 weight % (particularly 45–60%, and, more particularly, 46–53%) of a volatile silicone (especially a D5 cyclomethicone);
(b) 0.5–20 weight % (on a solids basis) (particularly 1–15% and, more particularly, 1–10%) of a non-emulsifying elastomer (also called cyclomethicone (and) dimethicone crosspolymer composition) as described below;
(c) 0.1–10 weight % of a of a superabsorbent powder with little or no tack upon wetting such as, for example, a water lock superabsorbent polymer selected from the group consisting of starch graft homopolymers and copolymers of poly(2-propenamide-co-2-propenioic acid) sodium salt (such as A 180 from Grain Processing Corp., Muscatine, Iowa);
(d) 0.01–0.5 weight % of a cooling agent selected from the group consisting of L-menthol; menthyl lactate; menthone glycerine; menthone glycerin acetal; (−)-isopulegol, N-ethyl-5-methyl-2-(1-methylethyl)-cyclohexanecarboxamide; N-ethyl-p-menthane-3-carboxzamide; 4-methyl-3-(1-pyrrolidinyl)-2[5H]-furanone; N,2,3-trimethyl-2-isopropylbutanamide (also known as 2-isopropyl-N,2,3-trimethylbutyramide); menthoxypropanediol; methanediol; vanillyl butyl ether; (particularly L-menthol and menthyl lactate);
(e) 0–20 weight % (particularly 1–15 weight % and more particularly 1–10 weight %) of an emollient or a mixture of two or more emollients;
(f) 0–30 weight % (particularly 0.1–30 weight %, more particularly 10–25weight % to get an antiperspirant effect) of an antiperspirant active based on an anhydrous, buffer-free antiperspirant active;
(g) 0–8 weight % (particularly 2–8 weight %) of polyethylene beads having a particle size in the range of 5–40 microns and a density in the range of 0.91–0.98 g/cm$^3$;
(h) 0–5 weight % (particularly 0.1–5 weight %) fragrance; and
(j) 0–5 weight % antimicrobial agent;
wherein the ratio of cooling agent to superabsorbent polymer is in the range of 1:50–1:2, more particularly in the range of 1:10–1:2.

It should be noted that the ratio of cooling agent to superabsorbent is an important feature of this invention. It is a cooling moderator that allows sufficient water to be released to activate the cooling agent while maintaining sufficient dryness to prevent the cooling agent from feeling too wet.

The compositions of the invention may be made in the form of soft solids.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula III:

Formula III wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4COOR^5$. The chain length for $R^4$ and $R^5$ can vary from 7 to 30 and can be saturated or unsaturated, straight chained or branched. Specific examples include isopropyl myristate, isopropyl palmitate, isopropyl stearate, isopropyl isostearate, butyl stearate, octyl stearate, hexyl laurate; cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, neopentyl glycol dioctanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristylinyristate.

(d) saturated and unsaturated fatty acids which are the carboxylic acids obtained by hydrolysis of animal or vegetable fats and oils. These have general structure $R^6COOH$ with the $R^6$ group having a carbon chain length between 7 and 30, straight chain or branched. Specific examples include lauric, myristic, palmitic, stearic, oleic, linoleic and behenic acid.

(e) saturated and unsaturated fatty alcohols (including guerbet alcohols) with general structure $R^7OH$ where $R^7$ can be straight or branched and have carbon length of 7 to 30. Specific examples include lauryl, myristyl, cetyl, isocetyl, stearyl, isostearyl, oleyl, ricinoleyl and erucyl alcohol;

(f) lanolin and its derivatives which are a complex esterified mixture of high molecular weight esters of (hydroxylated) fatty acids with aliphatic and alicyclic alcohols and sterols. General structures would include $R^8CH_2$—$(OCH_2CH_2)_nOH$ where $R^8$ represents the fatty groups derived from lanolin and n=5 to 75 or $R^9CO$—$(OCH_2CH_2)_nOH$ where $R^9CO$— represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.

(g) alkoxylated alcohols wherein the alcohol portion is selected from aliphatic alcohols having 2–18 and more particularly 4–18 carbons, and the alkylene portion is selected from the group consisting of ethylene oxide, and propylene oxide having a number of alkylene oxide units from 2–53 and, more particularly, from 2–15, Specific examples include PPG-14 butyl ether and PPG-53 butyl ether.

(h) silicones and silanes the linear organo-substituted polysiloxanes which are polymers of silicon/oxygen with general structure:

(1) $(R^{10})_3SiO(Si(R^{11})_2O)_xSi(R^{12})_3$ where $R^{10}$, $R^{11}$ and $R^{12}$ can be the same or different and are each independently selected from the group consisting of phenyl and C1–C60 alkyl;

(2) $HO(R^{14})_2SiO(Si(R^{15})_2O)_xSi(R^{16})_2OH$, where $R^{14}$, $R^{15}$ and $R^{16}$ can be the same or different and are each independently selected from the group consisting of phenyl and C1–C60 alkyl; or (3) organo substituted silicon compounds of formula $R^{17}Si(R^{18})_2OSiR^{19}_3$ which are not polymeric where $R^{17}$, $R^{18}$ and $R^{19}$ can be the same or different and are each independently selected from the group consisting of phenyl and C1–C60 alkyl optionally with one or both of the terminal R groups also containing an hydroxyl group. Specific examples include dimethicone, dimethiconol behenate, $C_{30-45}$ alkyl methicone, stearoxytrimethylsilane, phenyl trimethicone and stearyl dimethicone.

(i) mixtures and blends of two or more of the foregoing.

Emollients of special interest include C12–15 alkyl benzoate (FINSOLV TN from Finetex Inc., Elmwood Park, N.J.), isopropyl myristate; and neopentyl glycol diheptanoate.

The emollient or emollient mixture or blend thereof incorporated in compositions according to the present invention can, illustratively, be included in amounts of 0.1–20%, preferably 1–15%, more preferably 1–10%, by weight, of the total weight of the composition.

The elastomer is a non-emulsifying polysiloxane that does not contain any appreciable amount of polyoxyalkylenes, for example, polyoxyethylenes, and may be selected from the group consisting of:

(a) a cross-linked or partially cross-linked cyclomethicone (and) dimethicone crosspolymer (for example, DC 9040 or DC 9045 from Dow Corning Corp., Midland, Mich.);

(b) a cross-linked or partially cross-linked dimethicone/vinyldimethicone crosspolymer (for example, KSG-15 or USG-103 from Shin-Etsu Silicones of America, Akron Ohio);

(c) a cross-linked or partially cross-linked cyclomethicone (and) vinyldimethicone/methicone crosspolymer (for example, GE 1229 from General Electric Silicones, Waterford, N.Y.).

One particular type of elastomer is described in U.S. Pat. No. 5,654,362, incorporated by reference to the extent it defines non-emulsifying elastomers. These elastomers are prepared by a crosslinking reaction between (a) ≡Si—H containing polysiloxanes and (b) an alpha, omega-diene in the presence of a platinum catalyst and (c) a low molecular weight linear or cyclic polysiloxane. The elastomer can be swollen with the low molecular weight polysiloxane under a shear force. The ≡Si—H containing polysiloxane of part (a) is represented by compounds of formula $(R^{13})_3SiO(R^{14}_2SiO)_a(R^{15}HSiO)_bSi(R^{13})_3$, designated herein as type $A^1$, and compounds of the formula $H(R^{13})_2SiO(R^{14}_2SiO)_cSi(R^{13})_2H$ or formula $H(R^{13})_2SiO(R^{14}_2SiO)_a(R^{15}HSiO)_bSi(R^{13})_2H$, designated herein as $A^2$. In these formulas, $R^{13}$, $R^{14}$, and $R^{15}$ are alkyl groups with 1–6 carbon atoms, a is 0–250, b is 1–250, and c is 0–250. The molar ratio of compounds $A_1:A^2$ is 0–20, preferably 0–5. It is preferred that compounds of both types $A_1$ and $A^2$ be used. The alpha, omega diene in part (b) is a compound of the formula $CH_2=CH(CH_2)_xCH=CH_2$ where x is 1–20. Representative examples of suitable alpha, omega-dienes include 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene. Particular elastomers of interest of this type include DC-9040 and DC-9045, both from Dow Corning Corporation (Midland Mich.).

Another non-emulsifying elastomer described herein is a dimethicone/vinyldimethicone crosspolymer composition which: (1) is used at a concentration of 4–10% in cyclomethicone (particularly 4–7%, and, more particularly, 4–6.5%) (for example, where the cyclomethicone is a D4 or D5 cyclomethicone); (2) has a refractive index in the range of 1.392–1.402 at 25 degrees C.; and (3) has a viscosity in the range of 0.013–1×10⁴ Pascal seconds. Examples of these include KSG-15 and USG-103, both from Shin-Etsu Silicones of America (Akron, Ohio).

Note that the DC-9040 and DC-9045 products, and the KSG-15 and USG-103 products are normally sold in combination with cyclomethicone.

The antiperspirant active can be selected from the group consisting of any of the known antiperspirant active materials. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex ply and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Particular types of antiperspirant actives include aluminum zirconium trichlorohydrex and aluminum zirconium tetrachlorohydrex either with or without glycine. A particular antiperspirant active is aluminum trichlorohydrex gly such as AZZ-902 SUF (from Reheis Inc., Berkley Heights, N.J.) which has 95% of the particles less than 10 microns in size and AA ZG 7167 and AA ZG 7168 (from Summit Research Labs, Huguenot, N.Y.) which also has 95% of the particles less than 10 microns in size.

Another particular type of antiperspirant salt of interest is the group that has a low metal to chloride ratio such as in the range of 0.9–1.2:1. Examples of such salts are described in U.S. Pat. No. 6,375,937.

Antiperspirant actives can be incorporated into compositions according to the present invention in amounts in the range of 0.1–25% of the final composition, but the amount used will depend on the formulation of the composition. For example, at amounts in the lower end of the broader range (for example, 0.1–10% on an actives basis), a deodorant effect may be observed. At lower levels the antiperspirant active material will not substantially reduce the flow of perspiration, but will reduce malodor, for example, by acting as an antimicrobial material. At amounts of 10–25% (on an actives basis) such as 15–25%, by weight, of the total weight of the composition, an antiperspirant effect may be observed.

The antiperspirant active material is desirably included as particulate matter suspended in the composition of the present invention in amounts as described above, but can also be added as solutions or added directly to the mixture.

The polyethylene beads useful with this invention have a density in the range of 0.91–0.98 g/cm³ and a particle size in the range of 5–40 microns, with one particular type of polyethylene having a particle size of 20 microns. All particle sizes are averages. Several types of suitable polyethylene beads that are commercially available are MICROTHENE FN 510 from Equistar Chemicals LP (Houston, Tex.); and ACUMIST A-6 from Allied Signal Corp., Morristown, N.J.). It is believed that the polyethylene component contributes to the reduction in syneresis and is also responsible for giving the products a powdery feel as determined by trained sensory panels.

These compositions are soft solids made as suspensions and thickened or gelled by the elastomer component. While other thickeners may be used, the compositions of this invention will normally use the elastomer component as the only gellant. Of course various viscosities for a soft solid may be made depending on the amount of elastomer material and the amount of other ingredients used. One group having a more viscous form will have a viscosity in the range of 25,000–2,000,000 centipoise, particularly 50,000–1,000,000 centipoise, and suitable for use with an applicator with porous openings or slots such as those described in U.S. Ser. No. 9/191,897 (PCT 99/25570) incorporated by reference herein as to the description of the applicators. Another form will have a lower viscosity such as in the range of 20,000–200,000 centipoise and will be suitable for use with applicators requiring a thinner composition, for example roll-on applicators which have a rolling ball structure. For example, such roll-on applicators are described in U.S. Pat. Nos. 5,158,385 and 4,984,921. incorporated by reference herein as to the description of the applicators.

While various forms have been described, it is believed that the compositions made according to this inventions should preferably have a ratio of elastomer to antiperspirant active in the range of 1:2–1:20 in order to achieve the optimum improved efficacy and the improved stability that has been observed.

Compositions according to the present invention can be made by mixing the silicone gel material with, active ingredient(s) and optionally one or more of emollient(s), thickener(s) and fragrance. Mixing conditions and the use of heating will depend on what types of materials are being combined and; the melting points for those materials as are known to those skilled in the art. For example if soft solids, roll-ons or gels are being made, temperatures, in the range of room temperature or slightly higher (for example, 25–50 degrees C., particularly 23–30 degrees C.) may be used. For stick products and soft solid/cream products made with higher melting point materials (for example, high temperature waxes) temperatures from 25–85 degrees C. may be used. The mixture can be introduced into dispensing containers known to those skilled in the art including those for solids, gels, roll-ons, soft solids and creams. In one particular example, slotted dispensers may be used such as those known in the art, for example, those having a parallel row or rows of straight or curved slots or holes with a screw mechanism for forcing the composition through the top as the product is used.

Where the dispensing containers have a top surface with slots therein, the composition can be rubbed onto the skin from the top surface of the container (itself fed from a reservoir of product in the container) so as to deposit an adequate amount of the cosmetic composition on to the skin. The cosmetic composition, for example, an antiperspirant and/or deodorant in the form of a soft solid, can be extruded from inside the dispensing container through the slots or holes onto the top of the surface of the dispensing container, and from there may be applied to the skin in the axillary regions to deposit sufficient amounts of antiperspirant and/or deodorant active material to reduce body malodor and/or reduce perspiration in axillary regions of the human body.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application (a) values for n, m, etc. in formulas, molecular weights and degree of ethoxylation or propoxylation are averages; (b) temperatures are in degrees C. unless otherwise indicated; and (c) the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997). Mixing techniques used to make the compositions are those conventionally used in the art including those described above.

Examples 1A–6A

Preparation of Soft Solid With and Without Superabsorbent

The solvent components such as the volatile silicone (for example, cyclomethicone), non-volatile silicone (for example, phenyl trimethicone), and emollients (for example, C12–15 alkyl benzoate, neopentyl glycol diheptanoate, and isopropyl myristate) are added to a Hobart Mixer (Model N-50 from Hobart Corp., Troy, Ohio). The mixture is blended for about 5 minutes. The antiperspirant active is then added as a dry powder with continuous mixing for 15 minutes. The superabsorbent powder (if used) is now added and mixed for 10 minutes. The polyethylene beads are added and mixed for 10 minutes. The elastomer is then added and blended for an additional 15 minutes. The cooling agent/fragrance mixture is separately prepared by weighing L-Menthol and Menthyl lactate (Frescolat ML) into a small beaker, adding the fragrance and dissolving the solid menthol by gentle agitation at room temperature. The cooling agent/fragrance mixture is then added to the reaction vessel, blended for 5 minutes and transferred into suitable containers, such as those described above with straight or curved parallel slotted openings.

Batches of 500 gram size may be made with the types and amounts of ingredients listed in TABLE A. All amounts are in weight % based on the total weight of the composition. The antiperspirant active is AZZ 902 SUF (Reheis, Berkeley Heights, N.J.).

The polyethylene is Microthene FN510 (Equistar).
The cyclomethicone is DC 345 (Dow Corning).
The superabsorbent is A180 (Grain Processing Corp.)
The elastomer is DC 9040 (Dow Corning) which is 12–13% elastomer in cyclomethicone (DC 245 from Dow Corning). The amount of elastomer in the table may be back calculated to get the exact amount of elastomer and the additional amount of cyclomethicone.

TABLE A

| Ingredient | #1A | #2A | #3A | #4A | #5A | #6A |
|---|---|---|---|---|---|---|
| Neopentyl glycol diheptanoate | 0.50 | 0.50 | 0.50 | 0.50 | 0.50 | 0.50 |
| Cyclo-methicone | 5.80 | 0.80 | 6.30 | 1.30 | 3.30 | 3.80 |
| Phenyl trimethicone (DC 556) | 0.50 | 0.50 | 0.50 | 0.50 | 0.50 | 0.50 |
| Isopropyl myristate | 0.50 | 0.50 | 0.50 | 0.50 | 0.50 | 0.50 |
| C12–15 Alkyl-benzoate | 7.00 | 7.00 | 7.00 | 7.00 | 7.00 | 7.00 |
| Antiperspirant active | 25.00 | 25.00 | 25.00 | 25.00 | 25.00 | 25.00 |
| Polyethylene | 6.00 | 6.00 | 6.00 | 6.00 | 6.00 | 6.00 |
| Superabsorhent | 0 | 5.00 | 0 | 5.00 | 2.50 | 2.50 |
| Elastomer | 52.50 | 52.50 | 52.50 | 52.50 | 52.50 | 52.50 |
| Fragrance | 1.20 | 1.20 | 1.20 | 1.20 | 1.20 | 1.20 |
| L-Menthol | 0.40 | 0.40 | 0.20 | 0.20 | 0.40 | 0.20 |
| Menthyl lactate | 0.60 | 0.60 | 0.30 | 0.30 | 0.60 | 0.30 |
| Total | 100 | 100 | 100 | 100 | 100 | 100 |

We claim:

1. A stable, surfactant-free, soft solid cosmetic composition comprising:
   (a) 40–75 weight % of a volatile silicone;
   (b) 0.5–20 weight % of a non-emulsifying silicone elastomer (on a solids basis);
   (c) 0.1–10 weight % of a of a superabsorbent powder with little or no tack upon wetting;
   (d) 0.01–0.5 weight % of a cooling agent selected from the group consisting of L-menthol; menthyl lactate; menthone glycerine; menthone glycerin acetal; (–)- isopulegol, N-ethyl-5-methyl-2-(1-methylethyl)-cyclohexanecarboxamide; N-ethyl-p-menthane-3-carboxzamide; 4-methyl-3-(1-pyrrolidinyl)-2[5H]-furanone; N,2,3-trimethyl-2-isopropylbutanamide; menthoxypropanediol; methanediol; and vanillyl butyl ether;

(e) 0–20 weight % of an emollient or a mixture of two or more emollients;

(f) 0–30 weight % of an antiperspirant active based on an anhydrous, buffer-free antiperspirant active;

(g) 0–8 weight % of polyethylene beads having a particle size in the range of 5–40 microns and a density in the range of 0.91–0.98 g/cm$^3$;

(h) 0–5 weight % fragrance; and (i) 0–5 weight % of an antimicrobial agent;

wherein the ratio of cooling agent to superabsorbent polymer is in the range of 1:50–1:2.

2. A cosmetic composition as claimed in claim 1 which comprises 10–25 weight percent of the antiperspirant salt.

3. A cosmetic composition as claimed in claim 2 wherein the antiperspirant salt has a low metal to chloride ratio in the range of 0.9–1.2:1.

4. A cosmetic composition as claimed in claim 1 which comprises 2–8 weight % of the polyethylene beads.

5. A cosmetic composition as claimed in claim 1 which comprises 1–10 weight % of the emollient.

6. A cosmetic composition as claimed in claim 1 which comprises 1–15 weight % (on a solids basis) of a non-emulsifying silicone elastomer.

7. A cosmetic composition as claimed in claim 1 which comprises 46–53 weight % of a volatile silicone.

8. A cosmetic composition as claimed in claim 1 wherein the water lock superabsorbent polymer is a starch graft homopolymers and copolymers of poly(2-propenamide-co-2-propenioic acid) sodium salt.

* * * * *